United States Patent [19]

Olney

[11] Patent Number: 4,988,710

[45] Date of Patent: Jan. 29, 1991

[54] ARYL-CYCLOALKYL-ALKANOLAMINES FOR TREATMENT OF CHOLINERGIC NEUROTOXINS

[75] Inventor: John W. Olney, St. Louis, Mo.

[73] Assignee: Washington University, St. Louis, Mo.

[21] Appl. No.: 398,721

[22] Filed: Aug. 25, 1989

[51] Int. Cl.$^5$ .................. A61K 31/445; A61K 31/40
[52] U.S. Cl. .................... 514/318; 514/319; 514/408; 514/649; 548/419
[58] Field of Search ............ 424/10; 596/241; 514/649, 318

[56] References Cited

PUBLICATIONS

Läscher, J. Pharmacol. Exp. Therp., vol. 233, pp. 204–213, 1985.

Primary Examiner—Mukund J. Shah
Assistant Examiner—Deborah D. Carr
Attorney, Agent, or Firm—Haverstock, Garrett and Roberts

[57] ABSTRACT

A compound and method are disclosed for reducing neurotoxic effects (such as seizures and brain damage) caused by cholinergic agents such as soman (a nerve gas) and pilocarpine (a convulsant drug used to study the mechanisms of epilepsy). Effective treatment can be provided by administering an aryl-cycloalkylalkanolamine substance having the general formula:

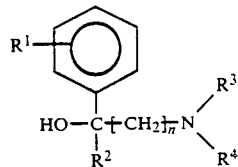

The compoudns procyclidine, biperiden, and trihexyphenidyl fall within this class of compounds. Although not previously recognized to be effective against soman or other cholinergic neurotoxins, all three representative compounds have been discovered to be highly effective against all cholinergic neurotoxins tested to data, even when administered after actual seizures begin.

12 Claims, No Drawings

ARYL-CYCLOALKYL-ALKANOLAMINES FOR TREATMENT OF CHOLINERGIC NEUROTOXINS

FIELD OF THE INVENTION

This invention is in the fields of pharmacology and neurology. It relates specifically to compounds and methods for reducing the neurotoxic effects of cholinergic agents.

BACKGROUND OF THE INVENTION

Researchers have tried to develop ways of protecting the mammalian brain against damage caused by certain types of convulsant drugs which fall within the class of "cholinergic neurotoxins" (discussed below). Two convulsant drugs of particular interest are (1) pilocarpine, which is of interest to researchers studying the causes and mechanisms of epilepsy (Clifford et al 1987; complete citations are provided below) and (2) a compound referred to as soman, a nerve gas that poses a threat in chemical warfare (McLeod et al 1984). Both of those substances can cause continuous seizure activity which persists for hours and causes disseminated brain damage, which typically is fatal unless adequately treated.

In trying to develop effective ways to protect mammalian brains against cholinergic neurotoxins, a substantial amount of effort has focused on tranquilizers and sedatives. Diazepam (sold under the trade name Valium) and phenobarbitol provide partial protection, but only at relatively high doses which are overly sedating, and such protection is unreliable unless the protective agent is administered prior to the convulsant (Clifford et al 1982; Fuller et al 1981). Obviously, pretreatment of front-line troops with heavily sedating doses of Valium would be infeasible for military reasons. Atropine provides some degree of protection against seizures induced by pilocarpine, but only if the atropine is administered prior to the pilocarpine (Honchar et al 1983). Since the nerve gas soman is a cholinesterase inhibitor, various efforts have been made to control its effects using cholinesterase reactivators (Goodman et al 1975). Such efforts provide unreliable results at best, and usually require pretreatment.

At least one published report states that a substance referred to as MK-801 (a glutamate antagonist, discussed below) provides some degree of protection against soman, if administered before soman exposure and if used in conjunction with other protective agents (Braitman et al 1988). However, as mentioned above, pretreatment to protect soldiers against nerve gas is rarely feasible. Perhaps even more importantly, recent research by the inventor of the subject application has discovered that when MK-801, phencyclidine, or ketamine were used in an effort to protect lab animals against pilocarpine, another major class of cholinergic neurotoxin, the seizure activity was made worse and the outcome was rapidly lethal. Although the reasons for those apparently conflicting results are not entirely clear, both sets of results suggest that interactions between the cholinergic and glutamate receptor systems may be relevant to efforts to provide an effective method for protecting the brain against cholinergic neurotoxins. The following sections provide background information on the cholinergic and glutamate receptor systems, and on various types of drugs which have been used to evaluate and control them.

Receptors, messenger molecules, agonists, and antagonists

The surfaces of nerve cells in the brain contain various types of receptor molecules. In general, a receptor molecule is a polypeptide which straddles a cell membrane. When a messenger molecule interacts with the exposed extracellular portion of the membrane receptor molecule, it triggers a difference in the electrochemical status of the intracellular portion of the receptor, which in turn provokes some response by the cell. The messenger molecule does not bond to the receptor; instead, it usually disengages from the receptor after a brief period and returns to the extracellular fluid. Most receptor molecules are named according to the messenger molecules which bind to them.

An "agonist" is any molecule, including the naturally occurring messenger molecule, which can temporarily bind to and activate a certain type of receptor. An agonist can cause the same effect as the natural messenger molecule, or in some cases it can cause a more intense effect (for example, if it has a tighter affinity for the receptor molecule and remains bound to the receptor for a prolonged period).

By contrast, an "antagonist" is a molecule which can block or reduce the effects exerted by the natural messenger molecule. This can happen in several different ways. A "competitive antagonist" binds to a certain type of receptor without triggering it, thereby preventing the natural messenger molecule from reaching and activating the receptor. A "non-competitive antagonist" functions in other ways. For example, a receptor referred to as the PCP receptor, which is triggered by molecules such as PCP or MK-801, apparently can override the effects of a different type of receptor, the NMDA receptor (both receptors are discussed below). Therefore, PCP and MK-801 are regarded as non-competitive antagonists for the NMDA receptor.

The role a certain molecule plays as an agonist or antagonist must be viewed with regard to a certain type of receptor. For example, while MK-801 is an antagonist for the NMDA receptor, it is an agonist for the PCP receptor. Most agonists and antagonists are xenobiotic drugs, i.e., they do not exist naturally in the body.

For more information on neurotransmitters, receptors in the brain and central nervous system, and agonists and antagonists which interact with brain cell receptors, see Adelman 1987.

The two classes of excitatory receptor molecules that are of interest with respect to the subject invention are referred to as "cholinergic" receptors and "glutamate" (also called "EAA") receptors, discussed below. Both types of receptors are present in the synaptic junctions that serve as pathways for impulses between nerve cells in the brain. They are believed to be the two main classes of excitatory receptors. Most other types of receptors in the brain involve inhibitory neurotransmitters.

Cholinergic receptors

Cholinergic receptors are activated by acetyl choline, a relatively small molecule released by certain types of brain cells. Cholinergic receptors are divided into two main classes: the muscarinic receptors (which are further subdivided into M1 and M2 receptors), and the nicotinic receptors.

After a molecule of acetyl choline performs its neurotransmitter function, it is quickly degraded by an enzyme called cholinesterase. Some types of toxins, including the nerve gas soman and some types of insecticides, generate toxic effects by inhibiting the cholinesterase enzyme. If that enzyme is disabled, an excess of acetyl choline accumulates in the extracellular fluid, where it causes uncontrolled firing of the nerve cells and results in severe neural damage, typically ending in death.

Pilocarpine acts in a different manner, as an agonist at cholinergic receptors. It can cause a severe syndrome consisting of continuous "clonic" seizure activity (seizure activity manifested by shaking; a "tonic" seizure is manifested by muscle rigidity) that often terminates in death. After an hour of such seizure activity, acute neuronal degeneration is evident (Clifford et al 1987). A high dose of pilocarpine (400 mg/kg subcutaneously) is usually required to cause this syndrome, and rats show considerable individual variability in sensitivity. However, it is possible to produce this cholinotoxic syndrome consistently with a low dose of pilocarpine (30 mg/kg) if it is preceded by a priming dose of lithium (Honchar et al 1983). Therefore, the lithium/pilocarpine syndrome has become a useful animal model for studying cholinergic neurotoxic mechanisms and seizure-related brain damage. Pilocarpine is also used in ophthalmology, where it can cause toxic effects if a patient is taking lithium for other reasons.

Glutamate receptors

Glutamic acid and aspartic acid are amino acids. Each contains two carboxylic acid groups. Either of those amino acids, and various analogs of those molecules, can trigger a class of receptors referred to as "excitatory amino acid" (EAA) receptors.

EAA receptors are also referred to as "glutamate" receptors, for several reasons. At the normal pH which exists in the brain, glutamic acid dissociates to form its ion, glutamate, which is naturally present in high concentrations inside the brain cells. Glutamate was the first molecule shown to trigger EAA receptors, and glutamate has been shown to trigger all three known subtypes of EAA receptors. It is suspected of being the natural transmitter at all EAA receptors.

There are three known types of glutamate receptors. One type is called the kainic acid (KA) receptor, since it can be triggered (in lab conditions) by kainic acid, a glutamate agonist which normally does not exist inside the brain. As mentioned above, kainic acid, a potent convulsant, is used in lab animals to study the mechanisms of epileptic seizures and epilepsy-related brain damage.

Another type of glutamate receptor is called the quisqualate (QUIS) receptor, since it can be triggered by quisqualic acid, another convulsant drug.

The third known type of glutamate receptor is called the NMDA receptor. The molecule N-methyl aspartate (NMA) is an analog of glutamate. Like all amino acids except glycine, it exists in two different isomers, the D and L forms. The D isomer of NMA—referred to as NMDA—exerts a powerful agonist effect on some glutamate receptors. Therefore, those receptors are referred to as NMDA receptors.

Each type of glutamate receptor controls a set of ion channel. For example, when an NMDA receptor is triggered by a glutamate molecule or a related agonist, it opens an ion channel which causes sodium and calcium to enter the cell while potassium is transported out of the cell.

Some molecules block the effects of glutamate on NMDA receptors, but they apparently do not act by directly blocking or occupying NMDA receptors; instead, they appear to activate other receptors (PCP receptors) which block the opening of the NMDA-receptor-controlled ion channels. In effect, they override the effects of the NMDA receptors, acting as "non-competitive antagonists." Such molecules include phencyclidine (PCP) and ketamine (see Anis et al 1983), and various phencyclidine derivatives (Berry et al 1983). Phencyclidine and ketamine reduce the excitatory effects of NMDA receptors, while they have no direct effect on the ion channels controlled by KA and QUIS receptors (Anis 1983).

The drug {(+)-5-methyl-10,11-dihydro-5H-dibenzo[a,d]-cyclohepten-5,10-imine maleate)}, commonly referred to as MK-801, is also a non-competitive antagonist of the NMDA receptor site (Wong 1986). It is a highly competitive agonist for the PCP receptor.

PCP, ketamine, and MK-801 are of interest because they can cross the blood-brain barrier and reach brain cells. Other NMDA antagonists such as D-$\alpha$-amino-5-phosphonopentanoate are also glutamate antagonists; however, since they cannot cross the blood-brain barrier, they are of little interest to neurologists.

Glutamate neurotoxicity

Under certain pathological conditions such as stroke and cardiac arrest, glutamate can act as a powerful neurotoxin capable of killing CNS neurons. Abnormal concentrations of glutamate in the extracellular fluid can generate acute "excitotoxic" effects which can kill or severely damage neurons in the CNS (Olney et al 1983). "Excitotoxic" implies that neurons are being killed, instead of merely implying that a toxin is present.

Glutamate normally exists at relatively high concentration (roughly 10 millimolar (mM)) inside axons. It is released by axon terminals very sparsely and in a very controlled manner, so that it directly enters a synaptic cleft and contacts a synaptic glutamate receptor. The only known mechanism for terminating the excitatory action of glutamate is to remove it from the synaptic cleft. This is normally achieved by energy-dependent transport systems that transport the extra-cellular glutamate back inside the axon terminals.

Certain types of low energy conditions can impair the ability of the glutamate transport system to control the amount of extracellular glutamate. Such conditions can include hypoglycemia (low blood sugar), ischemia (reduced blood flow, such as caused by stroke or heart attack), and hypoxia (low oxygen levels, caused by problems such as severe anemia, hemoglobin defects, carbon monoxide poisoning, and asphyxia). Under those conditions, brain cells release glutamate and, because of the energy deficiency, the transport systems are unable to move the glutamate back into the cells at an adequate rate.

This problem can be severely aggravated by the fact that initial glutamate release can stimulate further release of glutamate, which results in a cascade of extracellular glutamate accumulation and neurotoxic injury. It is believed that some of the neurotoxic injury associated with hypoxia or ischemia involves NMDA receptors, since such injury can be reduced or prevented by administering NMDA antagonists such as PCP, ketamine, and MK-801 (Lawrence et al 1987; Olney et al 1989).

It is also believed that in either the pilocarpine or soman cholinotoxic syndromes, persistent seizure activity is triggered by the excitatory activation of muscarinic cholinergic receptors, but much of the brain damage which ensues may be caused by seizure-mediated release of excessive glutamate at NMDA receptors. However, when NMDA antagonists such as phencyclidine, MK-801 or ketamine, which protect the brain against damage associated with kainic acid-induced seizures (Labruyere et al 1986), were administered to lithium/pilocarpine-treated rats by the inventor of the subject invention, a reaction was seen in which the seizure activity was made worse and the outcome was rapidly lethal. This unexpected finding suggests that an unknown mechanism operates in which phencyclidine, ketamine, or MK-801 interact with the cholinergic transmitter system to potentiate cholinergic activity.

Another potential disadvantage of using PCP, ketamine, or MK-801 for protecting against seizure-related neuropathology is that phencyclidine, the prototypic compound in this class, induces psychotomimetic effects in humans (Goodman et al 1975). Moreover, the inventor of the subject invention has recently discovered that phencyclidine, MK-801 and ketamine induce a neurodegenerative reaction in the posterior cingulate and retrosplenial cerebral cortex when administered in relatively low doses to adult rats (Olney et al 1989).

Aryl-cycloalkyl-alkanolamine compounds

Several aryl-cycloalkyl-alkanolamine drugs, including procyclidine, biperiden, and trihexyphenidyl, are known to have anti-cholinergic actions and have been identified for treatment of Parkinson's disease. Such compounds ameliorate the muscle rigidity and akinesia associated with Parkinsonism and extrapyramidal symptoms associated with neuroleptic drug treatment (Goodman et al 1975).

Some of these compounds have also been shown to have some degree of NMDA receptor antagonist properties, in that they reduce NMDA-induced neuronal degeneration in isolated chick embryo retinas (Olney et al 1987). Although these agents apparently compete with phencyclidine receptor ligands for binding at the PCP receptor, they are quite weak in PCP receptor activity compared to phencyclidine receptor ligands such as phencyclidine itself and MK-801.

The compound α-cyclohexyl-α-phenyl-1-pyrrolidinepropanol, commonly known as procyclidine, is described in U.S. Pat. No. 2,891,890 (Adamson 1959) as an anti-Parkinsonian drug. It is marketed under the trade name Kemadrin by Burroughs-Wellcome.

The compound commonly known as biperiden, α-bicyclo[2.2.1]-hept-5-en-2-yl-α-phenyl-1-piperidinepropanol, has been studied for its mood altering effects (Fleischhacker et al 1987) and for its interaction with brain muscarinic cholinoceptors (Syvalahti et al 1987). The hydrochloride salt of biperiden has been studied for its interaction with nicotine and oxotremorine in rat diaphragm (Das et al 1977). Biperiden is marketed under the trade name "Akineton" by Knoll.

The compound α-phenyl-α-tricyclo[2.2.1.02,6]-hept-3-yl-1-piperidinepropanol, commonly known as triperiden, is an anti-Parkinsonism agent which also reportedly has anti-viral properties (Schroeder et al 1985). It is marketed in Europe under the trade name "Norakin" by VEB Fahlberg-List (Magdeburg, West Germany).

The compound α-cyclohexyl-α-phenyl-1-piperidinepropanol, commonly known as trihexyphenidyl, is a known anti-Parkinsonian which has been studied for its effects in schizophrenic patients (Hitri et al 1987) and for its effects on memory in elderly patients McEvoy et al 1987). It is marketed under the trade name "Artane" by Lederle.

Various other aryl-cycloalkyl-alkanolamine compounds have also been studied for varying purposes. For example, U.S. Pat. No. 4,031,245 mentions the compound α-cyclopropyl-α-[3-(trifluoromethyl)phenyl]-1-piperidinepropanol and its hydrochloride derivative in a description of alkenyl and alkanylamines for treating depression. U.S. Pat. No. 3,553,225 mentions the compound α-phenyl-α-tricyclo[3.3.1.13,7]-dec-1-yl-1-piperidine-butanol in a description of adamantane derivatives as tranquilizers. West German Offen. No. 1,951,614, in a description of benzyl alcohol derivatives having sedative and ulcer-preventing properties, mentions the compounds α-(4-amino-3,5-dibromophenyl)-α-cyclohexyl-1-piperidinebutanol, α-(4-amino-3-chlorophenyl)-α-cyclo-hexylhexahydro-1H-azepine-1-butanol, α-(4-amino-3,5-dichlorophenyl)-α-cyclohexyl-hexahydro-1H-azepine-1-butanol, and α-(4-amino-3,5-dibromophenyl)-α-cyclohexyl-1,8,8-trimethyl-3-azabicyclo[3,2,1]octane-3-butanol. The compound α-[1,1'-biphenyl]-4-yl-α-cyclohexyl-1-piperidine propanol hydrochloride was mentioned in a study of the potential analgetic activity of some reduced biphenyl Mannich bases (Mann et al 1976).

It has not been proposed that any of these drugs could or should be useful either in animals or humans as a treatment to prevent seizures or seizure-related brain damage. Prior to this invention, there has been no adequate method or pharmacological agent for preventing or controlling seizures caused by cholinergic neurotoxins such as the nerve gas soman or insecticides, or for minimizing brain damage suffered from such compounds.

One object of this invention is to provide a method and pharmacological agent for protection against cholinergic neurotoxins, which can be administered after exposure to the toxin, to eliminate the requirement for pretreatment.

The subject invention surpasses that objective, and has been used with very effective results even after the onset of seizure symptoms.

SUMMARY OF THE INVENTION

A compound and method are disclosed for reducing neurotoxic effects (such as seizures and brain damage) caused by cholinergic agents such as soman (a nerve gas). Effective treatment can be provided by administering an aryl-cycloalkyl-alkanolamine substance having the general formula:

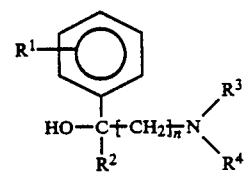

The compounds procyclidine, biperiden, and trihexyphenidyl fall within this class of compounds. Although not previously recognized to be effective against soman or other cholinergic neurotoxins, all three of those representative compounds have been discovered to be highly effective against all cholinergic neurotoxins tested to date, even when administered after actual seizures begin.

DESCRIPTION OF THE PREFERRED EMBODIMENTS

This invention relates to a compound and method for reducing neurotoxic effects (such as seizures and brain damage) caused by cholinergic agents such as soman (a nerve gas). Effective treatment can be provided by administering an aryl-cycloalkylalkanolamine represented by Formula I:

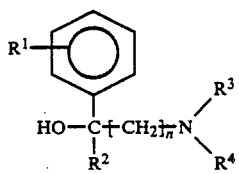

wherein $R^1$ is one or more groups independently selected from hydrido, halo, alkyl, acyl, hydroxyalkyl, haloalkyl, aminoalkyl, alkoxy, amino, alkylamino and acylamino; wherein $R^2$ is selected from hydrido, cycloalkyl, cycloalkenyl, halocycloalkyl, alkylcycloalkyl, acylcycloalkyl, hydroxycycloalkyl, haloalkylcycloalkyl, aminoalkylcycloalkyl, alkoxycycloalkyl, aminocycloalkyl, bicycloalkyl, bicycloalkenyl and tricycloalkyl wherein the bicycloalkyl, bicycloalkenyl and tricycloalkyl groups may be substituted with one or more groups selected from alkyl, halo, acyl, hydroxy, hydroxyalkyl, haloalkyl, acyl, alkoxy, amino and alkylamino; wherein each of $R^3$ and $R^4$ is independently selected from hydrido, alkyl, acyl, alkenyl, cycloalkyl, phenylalkyl, phenyl, aminoalkyl and alkylaminoalkyl; and wherein $R^3$ and $R^4$ may be taken together to form a cyclic group including the nitrogen atom of Formula I, and n is an integer selected from one through five.

During the research which led to this invention, seizures and seizure-related brain damage caused by pilocarpine or soman were effectively prevented in vivo tests using lab animals, by administration of several representative compounds of Formula I using the methods described in the Examples.

The compounds covered by Formula I includes several compounds that are commercially available, including:

α-cyclohexyl-α-phenyl-1-pyrrolidinepropanol (common name "procyclidine"), which has the following structure:

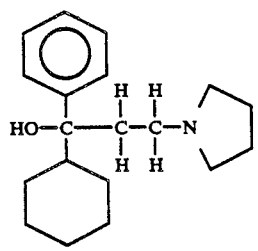

α-cyclohexyl-α-phenyl-1-piperidinepropanol (common name "trihexyphenidyl"), which has the following structure:

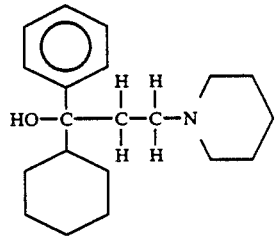

α-bicyclo[2.2.1]hept-5-en-2-yl-α-phenyl-1-piperidinepropanol (common name "biperiden"), which has the following structure:

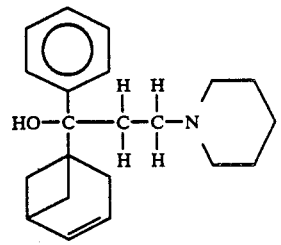

α-phenyl-α-tricyclo[2.2.1.0²,⁶]hept-3-yl-1-piperidinepropanol (common name "triperiden") which has the following structure:

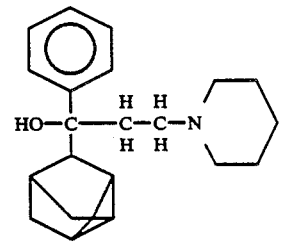

The following compounds also have chemical structures within the parameters described in Formula I:
3,3,5-trimethyl-α-phenyl-α-[2-(1-piperidinyl)ethylcyclohexanemethanol;
4-hydroxy-α-4-diphenyl-α-tricyclo[2.2.1.0²,⁶]hept-1-yl-1-piperidinepropanol;
α-cyclopropyl-α-[3-(trifluoromethyl)phenyl]-1-piperidinepropanol
α-phenyl-α-tricyclo[3.3.1.1³,⁷]dec-1-yl-1-piperidinebutanol;
α-phenyl-α-tricyclo[2.2.1.0²,⁶]hept-3-yl-1-piperidinepropanol
α-(4-amino-3,5-dibromophenyl)-α-cyclohexyl-1-piperidinebutanol;
α-(p-chlorophenyl)-α-cyclohexyl-1-piperidinepropanol
α-(4-amino-3-chlorophenyl)-α-cyclohexylhexahydro-1H-azepine-1-butanol;
α-cyclohexyl-α-(p-methoxyphenyl)-1-piperidinepropanol;
α-(4-amino-3,5-dichlorophenyl)-α-cyclohexylhexahydro-1H-azepine-1-butanol;
α-(4-amino-3,5-dibromophenyl)-α-cyclohexyl-1,8,8-trimethyl-3-azabicyclo[3.2.1]octane-3-butanol;
α-[1,1'-biphenyl]-4-yl-α-cyclohexyl-1-piperidinepropanol;

α-phenyl-α-tricyclo[3.3.1.1³,⁷]dec-1-yl-1-pyrrolidine-propanol
α-(3,3-dimethylbicyclo[2.2.1]hept-2-yl)-α-phenyl-1-piperidinepropanol;
α-cyclohexyl-4-hydroxy-α-4-diphenyl-1-piperidinepropanol
α-cyclopropyl-α-[3-(trifluoromethyl)phenyl]-1-piperidinepropanol;
α-cyclohexyl-α-phenyl-3-azabicyclo[3.2.2]nonane-3-propanol
α-[2-(diethylamino)ethyl]-α-phenylcyclohexanemethanol;
α-cyclopentyl-α-(3-(dimethylaminopropyl]-p-methoxybenzyl alcohol;
α-[3-(dimethylamino)propyl]-α-(α,α,α-trifluora-m-tolyl)-cyclohexanemethanol;
α-[3-(dimethylamino)propyl]-α-m-tolylcyclohexanemethanol;
α-(p-bromophenyl)-α-[3-(dimethylamino)propyl]cyclohexanemethanol;
α-(p-chlorophenyl)-α-[3-(dimethylamino)propyl]cyclohexanemethanol;
m-chloro-α-cyclopentyl-α-[3-(dimethylamino)propyl]-benzyl alcohol;
α-cyclopentyl-α-[3-(dimethylamino)propyl]benzyl alcohol;
α-[2-(dimethylamino)ethyl]-α-(p-methoxyphenyl)cyclohexanemethanol
α-[2-(diethylamino)ethyl]-α-(p-methoxyphenyl)cyclohexanemethanol;
α-(p-chlorophenyl)-α-[2-(dimethylamino)ethyl]cyclohexanemethanol;
α-(p-chlorophenyl)-α-[2-(diethylamino)ethyl]cyclohexanemethanol;
α-(p-bromophenyl)-α-[2-(dimethylamino)ethyl]cyclohexanemethanol
α-(p-bromophenyl)-α-[2-(diethylamino)ethyl]cyclohexanemethanol
α-[2-(diethylamino)ethyl]-α-phenylcyclohexanemethanol
α-(3-dimethylaminopropyl)-α-phenylcyclohexanemethanol
α-(2-dimethylaminoethyl)-α-phenyl-1-cyclohexene-1-methanol;
α-[5-[(2-diethylaminoethyl)methylaminol pentyl]-α-phenylcyclohexanemethanol;
α-[2-(dimethylamino)ethyl]-α-(p-propoxyphenyl)cyclohexanemethanol;
α-[2-(dimethylamino)ethyl]-α-(p-methoxyphenyl)cyclohexanemethanol;
α-[2-(dimethylamino)ethyl]-α-(p-ethoxyphenyl)cyclohexanemethanol;
α-[2-(dimethylamino)ethyl]-α-(p-isopropoxyphenyl)cyclohexanemethanol;
α-(p-butoxyphenyl)-α-[2-(dimethylamino)ethyl]cyclohexanemethanol;
α-[2-(dimethylamino)ethyl]-α-(p-isobutoxyphenyl)cyclohexanemethanol;
α-[2-(dimethylamino)ethyl]-α-(p-isopentyloxy)phenyl-cyclohexanemethanol;
α-[2-(dimethylamino)ethyl]-α-phenylcyclohexanemethanol;
α-[2-(dimethylamino)ethyl]-α-(p-pentyloxy)phenyl]cyclohexanemethanol;
α-(4-amino-3-bromophenyl)-α-[3-diethylamino)-propyl]cyclohexanemethanol;
α-(4-amino-3-chlorophenyl)-α-[3-diethylamino)-propyl]cyclohexanemethanol;
α-(4-amino-3,5-dichlorophenyl)-α-[3-dimethylamino)-propyl]cyclohexanemethanol;
α-(4-amino-3,5-dichlorophenyl)-α-[3-diethylamino)-propyl]cyclohexanemethanol;
α-(4-amino-3,5-dibromophenyl)-α-[3-dimethylamino)-propyl]cyclohexanemethanol;
α-(4-amino-3,5-dibromophenyl)-α-[3-(ethylmethylamino)propyl]cyclohexanemethanol;
α-(4-amino-3 5-dibromophenyl)-α-[3-(diethylamino)-propyl]cyclohexanemethanol;
α-(4-amino-3,5-dibromophenyl)-α-[3-(dipropylamino)propyl]cyclohexanemethanol;
α-(4-amino-3,5-dibromophenyl)-α-[3-(diallylamino)-propyl]cyclohexanemethanol;
α-(4-amino-3,5-dibromophenyl)-α-[3-(dibutylamino)-propyl]cyclohexanemethanol;
α-['4-amino-3,5-dibromophenyl)-α-[3-(cyclohexylmethylamino)propyl]cyclohexanemethanol;
α-(4-amino-3,5-dibromophenyl)-α-[3-(benzylmethylamino)propyl]cyclohexanemethanol;
α-(4-amino-3,5-dibromophenyl)-α-[3-(N-methylanilino)propyl]cyclohexanemethanol;
N-[2,6-dichlor-4-[1-cyclohexyl-4-(diethylamino)-1-hydroxybutyl]phenyl]acetamide;
α-cyclopropyl-α-[2-(dimethylamino)ethyl]benzenemethanol;
α-cyclopropyl-α-[3-(dimethylamino)propyl]benzenemethanol;
α-cyclopropyl-α-[2-(dimethylamino)ethyl]-4-methoxybenzenemethanol
α-cyclopropyl-α-(2-(dimethylamino)ethyl]-3-(trifluoromethyl)benzenemethanol
α-cyclopropyl-α-[2-(dimethylamino)ethyl]benzenemethanol;
α-cyclopropyl-α-[3-(dimethylamino)propyl]benzenemethanol;
α-cyclopropyl-α-[2-(dimethylamino)ethyl]-4-methoxybenzenemethanol;
α-cyclopropyl-α-[2-(dimethylamino)ethyl]-3-(trifluoromethyl)benzenemethanol;
N-[3-cyclopropyl-3-hydroxy-3-[3-(trifluoromethyl)-phenyl]propyl]-N-methylacetamide;
3-chloro-α-cyclopropyl-α-[2-(dimethylamino)ethyl]-benzenemethanol
α-cyclopropyl-α-[2-(diethylamino)ethyl]-4-(trifluoromethyl)benzenemethanol
α-cyclopropyl-α-[2-(diethylamino)ethyl]-3-(trifluoromethyl)benzenemethanol
α-[(dimethylamino)methyl]-α-(2-methylcyclopropyl)-benzenemethanol;
α-cyclopropyl-α-2-(dimethylamino)ethyl]-4-(trifluoromethyl)benzenemethanol;
α-cyclopropyl-α-[2-(diethylamino)ethyl]-3-(trifluoromethyl)benzenemethanol;
3-chloro-α-cyclopropyl-α-[2-(dimethylamino)ethyl]-benzenemethanol;
α-(2-diethylaminoethyl)-α-phenyl-5-norbornene-2-methanol;
α-(2-diethylaminoethyl)-α-phenyl-1-cyclohexene-1-methanol;
α-(3-dimethylaminopropyl)-α-phenyl-cyclohexanemethanol.

Any compound listed above may be tested by a routine screening process, as described in the Examples, to assess the effectiveness of that particular compound against cholinergic toxins such as soman or pilocarpine.

The term "hydrido" denotes a single hydrogen atom (H) which may be attached, for example, to a carbon atom or to an oxygen atom to form an hydroxyl group. The term "alkyl" embraces linear or branched radicals having one to about ten carbon atoms. The term "cycloalkyl" embraces radicals having three to about ten carbon atoms, such as cyclopropyl and cyclobutyl. The term "haloalkyl" embraces radicals wherein one or more of the alkyl carbon atoms is substituted with one or more halo groups, preferably selected from bromo, chloro and fluoro. Dihaloalkyl and polyhaloalkyl groups may be substituted with two or more of the same halo groups, or may have a combination of different halo groups. The terms "alkylol" and "hydroxylalkyl" embrace linear or branched alkyl groups having one to ten carbon atoms, any one of which may be substituted with one or more hydroxyl groups. The term "alkenyl" embraces linear or branched radicals having two to about ten carbon atoms and containing at least one carbon-carbon double bond. The terms "alkoxy" and "alkoxyalkyl" embrace linear or branched oxy-containing radicals having alkyl portions of one to ten carbon atoms, such as methoxy group. The "alkoxy" or "alkoxyalkyl" radicals may be further substituted with one or more halo atoms, such as fluoro, chloro or bromo, to provide haloalkoxy or haloalkoxyalkyl groups. Examples of other substituents forming compounds of Formula I are as follows:

| Substituent Name | Structure |
|---|---|
| alkylcycloalkyl | —⟨ ⟩—CH₃ |
| acylcycloalkyl | —⟨ ⟩—C(=O)—CH₃ |
| halocycloalkyl | —⟨ ⟩—Cl |
| hydroxycycloalkyl | —⟨ ⟩—OH |
| haloalkylcycloalkyl | —⟨ ⟩—CF₃ |
| aminoalkylcycloalkyl | —⟨ ⟩—CH₂—NH₂ |
| bicycloalkyl | (bicyclic structure) |
| bicycloalkenyl | (bicyclic structure with double bond) |
| tricycloalkyl | (tricyclic structure) |

Alkenyl and alkynyl groups may have one unsaturated bond, such as an allyl groups, or a plurality of unsaturated bonds, with such bonds adjacent, such as allene-type structures, in conjugation, or separated by several saturated carbons.

Included within the family of compounds of Formula I, are the tautomeric forms of the described compounds, isomeric forms including diastereomers, and the pharmaceutically-acceptable salts thereof.

The term "pharmaceutically-acceptable salts" embraces salts commonly used to form alkali metal salts and to form addition salts of free acids or free bases. Since the compounds of Formula I contain basic nitrogen atoms, such salts are typically acid addition salts. The nature of the salt is not critical, provided that it is pharmaceutically acceptable, and acids which may be employed to form such salts are well known to those skilled in this art. Examples of acids which may be employed to form pharmaceutically acceptable acid addition salts include such inorganic acids as hydrochloric acid, sulphuric acid and phosphoric acid, and organic acids such as maleic acid, succinic acid and citric acid. Other salts include salts with alkali metals or alkaline earth metals, such as sodium, potassium, calcium and magnesium. All of these salts may be prepared by conventional means from the corresponding compound of Formula I by reacting, for example, the appropriate acid with the compound of Formula I.

Methods of synthesis of representative compounds of Formula I are known. For example, synthesis of procyclidine and its salts are shown in U.S. Pat. Nos. 2,891,890 and 2,826,590. Synthesis of trihexyphenidyl hydrochloride is described in U.S. Pat. No. 2,682,543. Synthesis of biperiden is described in U.S. Pat. No. 2,789,110.

Administration of compounds within Formula I to humans can be by any technique capable of introducing the compounds into the bloodstream of a human patient, including oral administration, and by intravenous, intramuscular and subcutaneous injections. The active compound is usually administered in a pharmaceutically-acceptable formulation, although in some acute-care situations a compound of Formula I may be administered alone. Such formulations may comprise the active compound together with one or more pharmaceutically-acceptable carriers or diluents. Other therapeutic agents may also be present in the formulation. A pharmaceutically-acceptable carrier or diluent provides an appropriate vehicle for delivery of the active compound without introducing undesirable side effects. Delivery of the active compound in such formulations may be by various routes including oral, nasal, topical, buccal and sublingual, or by parenteral administration such as subcutaneous, intramuscular, intravenous and intradermal routes.

EXAMPLES

Example 1: Pilocarpine assay using procyclidine as pre-treatment

Adult male Sprague Dawley rats (300–400 g) were treated with lithium chloride (3 meq/kg subcutaneous (sc)), to potentiate the pilocarpine effect and reduce individual variability among the rats. One day later the experimental group was treated with procyclidine (75 mg/kg intraperitoneal (ip)). The control group was treated with an equivalent volume of saline. Thirty minutes later, both groups received a single treatment with pilocarpine (30 mg/kg sc).

Rats were observed over a 4 hour period for behavioral signs of neurotoxicity, including preconvulsive signs such as facial grimacing, head nodding, eye blinking, wet dog shakes, or evidence of convulsions, including rearing on hind limbs with clonic movements of the head and forelimbs. After 4 hours, they were anesthetized and perfused through the left cardiac ventricle and ascending aorta with an aldehyde fixative solution for 15 minutes, then the brains were removed from the skull and processed for histopathological evaluation by methods previously described for light and electron microscopy (Olney 1971).

The results were as follows: all of the rats in the saline control group, i.e., rats that received lithium/pilocarpine but not procyclidine, displayed the full behavioral syndrome of preconvulsive and convulsive symptoms with persistent seizure activity being present for the majority of the 4 hour observation period. All of these rats in the saline control group (n=6) had severe brain damage affecting the cerebral cortex, hippocampus, amygdala, piriform cortex, thalamus, lateral septum and substantia nigra. None of the treated rats (lithium/pilocarpine and procyclidine) displayed either preconvulsive or convulsive signs, and none (n=6) sustained brain damage.

Example 2: Pilocarpine assay using procyclidine as post-treatment

In a second experiment, all conditions were the same except that the procyclidine (75 mg/kg i.p.) or saline was not administered until 30 min after pilocarpine. All of the rats in the saline control group (n=6) exhibited a full behavioral syndrome, including persistent seizures and disseminated brain damage.

Most of the rats in the treatment group had begun to seize before procyclidine was administered, but all convulsive behavior disappeared within 10 minutes after procyclidine administration and all of these rats (n=6) escaped brain damage.

Prior research on receptor binding data had suggested that procyclidine interacts weakly with phencyclidine receptors (Olney et al 1987). In addition, recent research by the inventor of the subject application (Olney 1989) indicated that phencyclidine and MK-801 can cause vascular cytopathological changes in the posterior cingulate and retrosplenial cerebral cortices. The correlation of those findings suggests that procyclidine might also cause some degree of PCP-like toxicity. To evaluate that possibility, the affected brain regions were examined in the rats (n=12) from the treatment groups in both of the experiments described above (i.e., rats that received procyclidine either before or after the pilocarpine). There was no evidence of the vascular cytopathology that occurs following phencyclidine or MK-801 treatment.

Example 3: Soman assay using procyclidine as post-treatment

A major problem in studying the soman cholinotoxic syndrome is the marked individual variation in sensitivity of experimental animals. Some adult rats develop status epilepticus (persistent seizures) within 5-15 minutes after receiving a dose of soman in the range of 90-125 ug/kg (micrograms/kilogram) i.p. Those animals typically sustain severe brain damage and die within 1 to 6 hours. However, other rats can tolerate much higher doses of soman without exhibiting seizures or brain damage and such animals survive treatment without any apparent untoward effects. Administering lithium chloride 24 hours prior to soman causes a moderate, but consistent, increase in the percentage of animals susceptible to soman neurotoxicity.

In a study to evaluate the possibility that procyclidine might protect against the neurotoxic effects of soman, adult male Sprague Dawley rats (350–425 g) were pre-treated with lithium chloride (3 mg/kg sc) and 24 hrs later given soman (125 ug/kg sc) and observed for symptoms. Animals that began convulsing were treated immediately either with saline (control group) or a single dose (75 mg/kg i.p.) of procyclidine (treatment group). Animals that did not convulse received no further treatment.

All animals were anesthetized and killed 4 hours after soman treatment and their brains examined histologically by methods described above. Rats that did not seize (n=28) did not have any brain pathology. All rats that seized and received saline (n=8) had severe disseminated brain damage. Rats that seized and received procyclidine (n=12), stopped seizing within 5 to 15 minutes; all of these rats escaped brain damage.

In a separate experiment, atropine, which like procyclidine is classified as an anti-cholinergic drug, was substituted for procyclidine in the above protocol. At doses up to 100 mg/kg i.p., atropine conferred no protection against soman neurotoxicity.

Example 4: Soman assay using selected susceptible rats

In an additional experiment, the neuroprotective properties of procyclidine were exploited to establish a colony of rats selectively bred for increased susceptibility to soman neurotoxicity. Adult male and female rats were challenged with soman. Those that responded with seizures (n=8) were identified as soman-sensitive and were treated with procyclidine which protected them, allowing them to survive and serve as breeding stock.

The first generation offspring of soman-sensitive male/female matings were challenged with soman and found to have a substantially increased rate of soman sensitivity (increased from 40% to 80%), even though lithium pretreatment was not used. Administration of procyclidine to these animals (n=8) when they started seizing, consistently caused cessation of seizures and protection against brain damage.

Thus, if experimental animals from the above studies are combined, the total number of rats protected against soman neurotoxicity by administration of procyclidine following onset of convulsive symptoms is 28. Although lithium pretreatment was employed in the first experiment, rats in the latter two experiments (n=16) received soman without lithium pretreatment. Therefore, either in the presence or absence of lithium, procyclidine provides effective protection against soman neurotoxocity.

Example 5: Treatment with Biperiden or Trihexyphenidyl

Preliminary tests using a small number of rats were performed to determine whether biperiden or trihexyphenidyl were effective against a cholinergic neurotoxin. Rats were subjected to lithium priming and pilocarpine exposure as described in Example 2, and rats that showed seizure activity were treated with either biperiden or trihexyphenidyl. In all such rats, seizure activity ceased, and histological examination did not indicate any brain damage.

Although this invention has been described with respect to specific embodiments, the details of these embodiments are not to be construed as limitations. Various equivalents and modifications may be made without departing from the spirit and scope of this invention, which is limited only by the claims which follow.

REFERENCES

Adelman, G. (ed.), *Encyclopedia of Neurosciences* (Birkhauser, Boston, 1987).

Anis, N.A. et al, "The Dissociative Anaesthetics, Ketamine and Phencyclidine, Selectively Reduce Excitation of Central Mammalian Neurons by N-Methyl-Asparate", *Br. J. Pharmacol.* 79: 565 (1983).

Berry, S. D., et al, "Stereoselective Effects of Two Phencyclidine Derivatives on N-Methylaspartate Excitation of Spinal Neurones in the Cat and Rat", *Eur. J. Pharm.* 96: 261 (1983).

Braitman, D. J., et al, "MK-801 protects against seizures and brain damage induced by the cholinesterase inhibitor soman," *Neurosci. Abstr.* 14: 240 (1988).

Clifford, D. B., et al, "Effect of anti-convulsant drugs on kainic acid induced epileptiform activity," *Exp. Neurol.* 76: 156 (1982).

Clifford D. B., Olney, J. W., Maniotis, A., Collins, R. C. and Zorumski, C. F. "The functional anatomy and pathology of lithium-pilocarpine and high-dose pilocarpine seizures." *Neurosci.* 23: 953–968 (1987).

M. Das et al, *Toxicol. Appl. Pharmacol.* 39(1): 149–152 (1977).

Fleischhacker, W. W., et al, *J. Affective Disorder* 12(2): 153–157 (1987).

Fuller, T. A. and Olney, J. W., "Only certain anticonvulsants protect against kainic acid neurotoxocity," *Neurobiol. Toxicol. and Teratol.* 3: 355–361 (1981).

Goldman, M. E., et al, "Differentiation of [3H]Phencyclidine and (+)-[3H]SKF-10,047 Binding Sites in Rat Cerebral Cortex", *FEBS Lett.* 170: 333–336 (1985).

Goodman, L. S. and Gilman, A., *The Pharmacological Basis of Therapeutics*, 5th ed., (Macmillan, NY, 1975).

Hitri, A., et al, *Psychopharmacol. Bull.* 23(1): 33–37 (1987).

Honchar, M. P., Olney, J. W. and Sherman, W. R., "Systemic cholinergic agents induce seizures and brain damage in lithium-treated rats," *Science* 220: 323–325 (1983).

Labruyere, J., et al, "Phencyclidine and ketamine protect against seizure-related brain damage," *Neurosci. Abstr.* 12: 344 (1986).

Lawrence, J. J., Fuller, T. A., and Olney, J. W., "MK-801 and PCP protect against ischemic neuronal degeneration in the gerbil hippocampus," *Neurosci. Abstr.* 13: 1079 (1987).

Mann, N., et al, *Arch. Pharm. (Weinheim, Ger.)* 309(4): 320–325 (1976).

Maragos, W., et al, "High Correlation Between the Localization of [3H]TCP Binding and NMDA Receptors," *Eur. J. Pharmacol.* 123: 173–174 (1986).

McEvoy, J. P., et al, *Psychopharmacol. Bull.* 23(1): 30–32 (1987).

McLeod, C. G., et al, "Acute neuropathology in soman-poisoned rats," *Neurotoxicology* 5: 53–58 (1984).

Olney, J. W., "Glutamate-induced neuronal necrosis in the infant mouse hypothalamus: an electron microscopic study," *J. Neuropathol. Exp. Neurol.* 30: 75–90 (1971).

Olney, J. W., "Excitotoxins: an overview," in *Excitotoxins*, Fuxe, K., et al, Eds. (Macmillan, London) pp 82–96 (1983).

Olney, J. W., et al, "The Anti-Excitotoxic Effects of Certain Anesthetics, Analgesics and Sedative Hypnotics," *Neuroscience Letters* 68: 29–34 (1986).

Olney, J. W., et al, "Anti-Parkinsonian agents are phencyclidine agonists and N-methyl aspartate antagonists," *Eur. J. Pharmacol.* 142: 319–320 (1987).

Olney, J. W., et al, "MK-801 prevents hypobaric-ischemic neuronal degeneration in infant rat liver," *J. Neurosci.* 9: 1701 (1989).

Olney, J. W., et al, "Pathological changes induced in cerebrocortical neurons by phencyclidine and related drugs." *Science* 244: 1360–1362 (1989).

Quirion, R., "Phencyclidine (Angel Dust)/Sigma Opiate' Receptor: Visualization by Tritium-Sensitive Film," *Proc. Nat'l. Acad. Sci. U.S.A.* 78: 5881 (1981).

Rothman, S. M., and Olney, J. W., "Glutamate and the Pathophysiology of Hypoxia-Ischemic Brain Damage," *Annals of Neurology* 19(2): (1986).

Schroeder, C., et al, *Antiviral Res. Suppl.* 1: 95–99 (1985).

Snell, L. D., et al, "Antagonism of NMDA-Induced Transmitter Release In The Rat Striatum By Phencyclidine-Like Drugs And Its Relationship To Turning Behavior," *J. Pharmacol. Exp. Ther.* 235: 50–56, (1985).

Syvalahti, E. K. G., et al, *Pharmacol. Toxicol. (Copenhagen)* 60(1): 66–69 (1987).

Wong, E. H. F., et al, "The Anticonvulsant MK-801 Is A Potent N-Methyl-D-Aspartate Antagonist," *Proc. Nat'l. Acad. Sci U.S.A.* 83: pp. 7104–7108 (September 1986).

I claim:

1. A method for reducing the neurotoxic effects of cholinesterase inhibitors, which method comprises treating a susceptible mammal which is to be protected from neurotoxic brain damage that would otherwise be caused by a cholinesterase inhibitor with a therapeutically-effective amount of a compound of the formula:

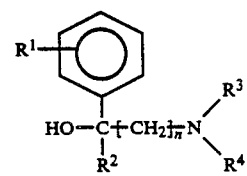

wherein $R^1$ is one or more groups independently selected from hydrido, halo, alkyl, acyl, hydroxyalkyl, haloalkyl, aminoalkyl, alkoxy, amino, alkylamino and acylamino; wherein R² is selected from hydrido, cycloalkyl, cycloalkenyl, halocycloalkyl, alkylcycloalkyl, acylcycloalkyl, hydroxycycloalkyl, haloalkylcycloalkyl, aminoalkylcycloalkyl, alkoxycyclo-alkyl, aminocycloalkyl, bicycloalkyl, bicycloalkenyl and tricycloalkyl wherein the tricycloalkyl, bicyclo-alkenyl and tricycloalkyl groups may be substituted with one or more groups selected from alkyl, halo, acyl, hydroxy, hydroxyalkyl, haloalkyl, acyl, alkoxy, amino and alkylamino; wherein each of R³ and R⁴ is independently selected from hydrido, alkyl, acyl, alkenyl, cycloalkyl, phenylalkyl, phenyl, aminoalkyl and alkylaminoalkyl; and wherein R³ and R⁴ may be taken together to form a cyclic group including the nitrogen atom of Formula I, and n is an integer selected from one through five.

2. A method of claim 1, wherein said compound is selected from the group consisting of:
α-cyclohexyl-α-phenyl-1-pyrrolidinepropanol (common name "procyclidine")
α-cyclohexyl-α-phenyl-1-piperidinepropanol (common name "trihexyphenidyl");
α-bicyclo[2.2.1]hept-5-en-2-yl-α-phenyl-1-piperidinepropanol (common name "biperiden");
α-phenyl-α-tricyclo[2.2.1.0²,⁶]hept-3-yl-1-piperidinepropanol (common name "triperiden");
and pharmaceutically acceptable salts of the compounds listed above.

3. A method of claim 1, wherein said compound comprises an analog of α-cyclohexyl-α-phenyl-1-pyrrolidinepropanol (common name "procyclidine") which is effective in reducing neurotoxic effects of cholinesterase inhibitors.

4. A method of claim 1, wherein said compound comprises an analog of α-cyclohexyl-α-phenyl-1-piperidinepropanol (common name "trihexyphenidyl") which is effective in reducing neurotoxic effects of cholinesterase inhibitors.

5. A method of claim 1, wherein said compound comprises an analog of α-bicyclo[2.2.1]hept-5-en-2-yl-α-phenyl-1-piperidinepropanol (common name "biperiden") which is effective in reducing neurotoxic effects of cholinesterase inhibitors.

6. A method of claim 1, wherein said compound comprises an analog of α-phenyl-α-tricyclo-[2.2.1.0²,⁶]hept-3-yl-1-piperidinepropanol (common name "triperiden") which is effective in reducing neurotoxic effects of cholinesterase inhibitors.

7. An article of manufacture, comprising packaging material and a pharmaceutical agent contained within said packaging material, wherein said pharmaceutical agent is therapeutically effective for reducing neurotoxic effects of at least one cholinesterase inhibitor, and wherein said packaging material comprises a label which indicates that said pharmaceutical agent can be used for reducing neurotoxic brain damage that might otherwise be caused by at least one cholinesterase inhibitor, and wherein said pharmaceutical agent comprises a compound of the formula:

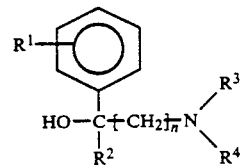

wherein R¹ is one or more groups independently selected from hydrido, halo, alkyl, acyl, hydroxyalkyl, haloalkyl, aminoalkyl, alkoxy, amino, alkylamino and acylamino; wherein R² is selected from hydrido, cycloalkyl, cycloalkenyl, halocycloalkyl, alkylcycloalkyl, acylcycloalkyl, hydroxycycloalkyl, haloalkylcycloalkyl, aminoalkylcycloalkyl, alkoxycyclo-alkyl, aminocycloalkyl, bicycloalkyl, bicycloalkenyl and tricycloalkyl wherein the bicycloalkyl, bicyclo-alkenyl and tricycloalkyl groups may be substituted with one or more groups selected from alkyl, halo, acyl, hydroxy, hydroxyalkyl, haloalkyl, acyl, alkoxy, amino and alkylamino; wherein each of R³ and R⁴ is independently selected from hydrido, alkyl, acyl, alkenyl, cycloalkyl, phenylalkyl, phenyl, aminoalkyl and alkylaminoalkyl; and wherein R³ and R⁴ may be taken together to form a cyclic group including the nitrogen atom of Formula I, and n is an integer selected from one through five.

8. An article of manufacture of claim 7, wherein said pharmaceutical agent is selected from the group consisting of:
α-cyclohexyl-α-phenyl-1-pyrrolidinepropanol (common name "procyclidine")
α-cyclohexyl-α-phenyl-1-piperidinepropanol (common name "trihexyphenidyl");
α-bicyclo[2.2.1]hept-5-en-2-yl-α-phenyl-1-piperidinepropanol (common name "biperiden");
α-phenyl-α-tricyclo[2.2.1.0²,⁶]hept-3-yl-1-piperidinepropanol (common name "triperiden");
and pharmaceutically acceptable salts of the compounds listed above.

9. An article of manufacture of claim 7, wherein said pharmaceutical agent is an analog of α-cyclohexyl-α-phenyl-1-pyrrolidinepropanol (common name "procyclidine") which is effective in reducing neurotoxic effects of cholinesterase inhibitors.

10. An article of manufacture of claim 7, wherein said pharmaceutical agent is an analog of α-cyclohexyl-α-phenyl-1-piperidinepropanol (common name "trihexyphenidyl") which is effective in reducing neurotoxic effects of cholinesterase inhibitors.

11. An article of manufacture of claim 7, wherein said pharmaceutical agent is an analog of α-bicyclo[2.2.1-]hept-5-en-2-yl-α-phenyl-1-piperidinepropanol (common name "biperiden") which is effective in reducing neurotoxic effects of cholinesterase inhibitors.

12. An article of manufacture of claim 7, wherein said pharmaceutical agent is an analog of α-phenyl-α-tricyclo-[2.2.1.0²,⁶]hept-3-yl-1-piperidinepropanol (common name "triperiden") which is effective in reducing neurotoxic effects of cholinesterase inhibitors.

* * * * *

UNITED STATES PATENT AND TRADEMARK OFFICE
CERTIFICATE OF CORRECTION

PATENT NO. : 4,988,710
DATED : January 29, 1991
INVENTOR(S) : John W. Olney

It is certified that error appears in the above—identified patent and that said Letters Patent is hereby corrected as shown below:

IN COLUMN 1, Line 5, the following section should be added:

--<u>Government Support</u>
This invention was made with government support under Contract DAMD17-86-C-6010 awarded by the U.S. Department of the Army. The government has certain rights in this invention.--

In the ABSTRACT, on the line following the chemical formula, the word "compoudns" should read --compounds--.

Signed and Sealed this

Fourth Day of August, 1992

Attest:

DOUGLAS B. COMER

*Attesting Officer*     *Acting Commissioner of Patents and Trademarks*